United States Patent
Fearnot et al.

(10) Patent No.: US 9,931,439 B2
(45) Date of Patent: Apr. 3, 2018

(54) MODIFIABLE MEDICAL GRAFTS AND RELATED METHODS AND APPARATUSES

(71) Applicants: Cook Biotech Incorporated, West Lafayette, IN (US); Cook Medical Technologies LLC, Bloomington, IN (US); Muffin Incorporated, West Lafayette, IN (US)

(72) Inventors: Neal E. Fearnot, West Lafayette, IN (US); Michael C. Hiles, West Lafayette, IN (US); Jeremy Metz, Lafayette, IN (US); F. Joseph Obermiller, West Lafayette, IN (US); Andrew J. Kaucher, Lafayette, IN (US); Steven Charlebois, West Lafayette, IN (US)

(73) Assignees: Cook Biotech Incorporated, West Lafayette, IN (US); Muffin Incorporated, West Lafayette, IN (US)

( * ) Notice: Subject to any disclaimer, the term of this patent is extended or adjusted under 35 U.S.C. 154(b) by 57 days.

(21) Appl. No.: 14/088,606

(22) Filed: Nov. 25, 2013

(65) Prior Publication Data
US 2014/0188250 A1 Jul. 3, 2014

Related U.S. Application Data

(63) Continuation of application No. PCT/US2012/066263, filed on Nov. 21, 2012.
(Continued)

(51) Int. Cl.
*A61F 2/02* (2006.01)
*A61L 27/60* (2006.01)
(Continued)

(52) U.S. Cl.
CPC ............ *A61L 27/60* (2013.01); *A61F 2/0063* (2013.01); *A61F 2/02* (2013.01); *A61L 27/3633* (2013.01);
(Continued)

(58) Field of Classification Search
CPC .......... A61F 2/105; A61F 2/08; A61F 2/0894; A61F 2/0063; A61F 2/02;
(Continued)

(56) References Cited

U.S. PATENT DOCUMENTS

| 6,001,123 A | 12/1999 | Lau |
| 2006/0100478 A1 * | 5/2006 | Connors .................... A61F 2/02 600/29 |

(Continued)

FOREIGN PATENT DOCUMENTS

GB 2 451 785 2/2009

*Primary Examiner* — Melanie Tyson
(74) *Attorney, Agent, or Firm* — Woodard, Emhardt, Moriarty, McNett & Henry, LLP

(57) ABSTRACT

Described are medical graft materials and devices which can be usefully modified with liquid additives such as cell suspensions, bioactive agents, or combinations of these. The medical graft materials and devices can have a first outer surface and a second outer surface and can define an internal chamber between the first outer surface and the second outer surface. The medical graft materials and devices can also have at least one region of the graft material interrupting the chamber and surrounded by the chamber. Also described are methods for making and using these medical graft materials and devices.

26 Claims, 5 Drawing Sheets

Related U.S. Application Data

(60) Provisional application No. 61/563,600, filed on Nov. 24, 2011.

(51) Int. Cl.
    *A61F 2/00*     (2006.01)
    *A61L 27/36*     (2006.01)
    *A61L 27/38*     (2006.01)

(52) U.S. Cl.
    CPC ....... *A61L 27/38* (2013.01); *A61F 2002/0072* (2013.01); *A61F 2210/0076* (2013.01); *A61F 2250/0003* (2013.01); *A61F 2250/0068* (2013.01)

(58) Field of Classification Search
    CPC ...... A61F 2002/0086; A61F 2002/0072; A61F 2210/0076; A61F 2250/0003; A61F 2250/0068; A61L 27/60; A61L 27/3633; A61L 27/367; A61L 27/38; A61L 27/3826; A61L 27/3873

See application file for complete search history.

(56) References Cited

U.S. PATENT DOCUMENTS

| | | | |
|---|---|---|---|
| 2007/0123977 A1 | 5/2007 | Cottone et al. | |
| 2008/0065229 A1* | 3/2008 | Adams | A61F 2/0063 623/23.75 |
| 2008/0107750 A1 | 5/2008 | Hodde et al. | |
| 2010/0155282 A1 | 6/2010 | Govil et al. | |
| 2010/0249947 A1* | 9/2010 | Lesh | A61L 27/16 623/23.74 |
| 2011/0264119 A1* | 10/2011 | Bayon | A61L 27/20 606/151 |
| 2012/0016491 A1* | 1/2012 | Matheny | A61K 35/12 623/23.72 |

\* cited by examiner ent No. PCT/US2012/066263, filed Nov. 21, 2012, which
MODIFIABLE MEDICAL GRAFTS AND RELATED METHODS AND APPARATUSES

REFERENCE TO RELATED APPLICATION

This application is a continuation of International Application No. PCT/US2012/066263, filed Nov. 21, 2012, which claims the benefit of priority of U.S. Provisional Patent Application Ser. No. 61/563,600 filed Nov. 24, 2011, each of which is hereby incorporated by reference in its entirety.

BACKGROUND

The present invention relates in certain of its aspects to medical devices and methods, for example involving medical graft materials that can be modified by the addition of cells or other substances, and to related kits and methods of use and preparation.

Medical grafts and implants have demonstrated significant promise to improve medical treatments for patients across a broad variety of conditions or injuries. One area of study has been that of implantable graft materials that contain additives such as bioactive substances or viable cells from the patient or from other sources. With regard to the harvest and re-introduction of cells or other biologic substances from the patient, termed autologous treatments, methods and systems are known for treating tissue samples from the patient to result in a cellular and/or other biological preparation that can be re-introduced to the patient. In related areas, cells or biologic substances obtained from donors other than the patient, sometimes embodied in stable cell lines or purified extracts, have also been known or proposed for introduction into the patient by themselves or with other implant materials.

In certain modes of use, cells or other substances to be introduced into the patient can be combined with a graft material to form an implantable graft. In respect of cellular grafts, sometimes these involve a culture period in which the number of cells is expanded after application to the graft material. Other modes of using cells do not involve such expansion. Rather, the cells are applied to the graft and implanted without a culture period.

Despite demonstrated promise, the clinical implementation of graft materials has been slow in many areas. Needs exists for more convenient and/or effective ways or materials for combining cells or other modifying substances with graft materials. In certain of its aspects, the present invention is addressed to these needs.

SUMMARY

In certain aspects, the present invention provides unique medical graft materials. These graft material can define internal chambers or other voids within the graft material which can be used to receive liquid additives, potentially combined with thru-holes in the graft material which can for example serve to pass biological fluids from one side of the graft material to the other after administration of the graft material to a patient.

In additional aspects, the invention provides advantageous arrangements of graft materials with other device or apparatus features such as liquid input ports or passages, trays, handle structures, and/or other features. In certain embodiments, a tray enclosure is provided that compresses the graft material in selected regions. This compression pattern can serve to facilitate defining a path of fluid flow or collection within the graft material. Additionally or alternatively, the tray enclosure can define a liquid capture well or drain region, to capture fluid that passes through a liquid permeable graft material, for example depositing cells or other bioactive materials on the graft material during that passage through the graft material.

Still additional features and embodiments of the invention as well as advantages associated therewith will be apparent to those of ordinary skill in the art from the descriptions herein, including the appended claims.

DETAILED DESCRIPTION

Figure 1:
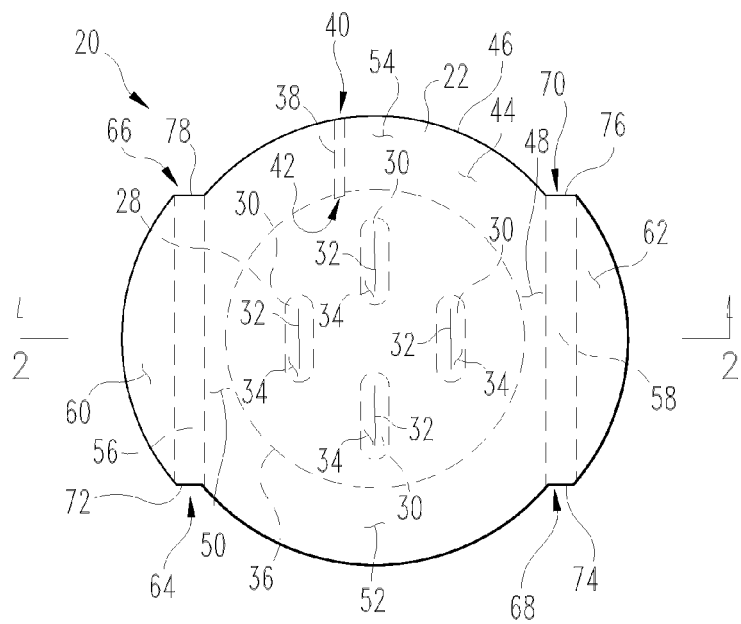
FIG. 1 provides a top view of a graft material according to one embodiment of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As disclosed above, the present invention provides materials and devices that are useful as medical grafts, apparatuses including the same, and related methods of preparation and use.

Referring now to FIGS. 1 through 8, illustrative embodiments will be described. It will be understood that the invention is not limited to these illustrative embodiments; rather a wide variety of additional designs for the disclosed graft materials and devices will be readily envisioned and practicable by those skilled in the art from the disclosure herein.

Figure 2:
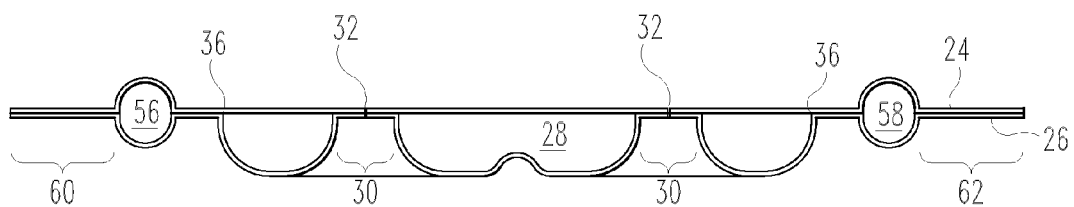
FIG. 2 provides a cross-sectional view taken along line 2-2 of FIG. 1 and viewed in the direction of the arrows.

Generally, shown in FIGS. 1 and 2 are a top view and a cross sectional view, respectively, of a modifiable medical graft 20. Medical graft 20 includes a graft material body 22 with several unique features. Graft body 22 in the illustrative embodiment is a laminate structure including a first sheet material 24 laminated to a second sheet material 26 (FIG. 2). The sheets 24 and 26 are joined to one another in selective areas and left unjoined in other areas. In a first unjoined region the sheets 24 and 26 define an interior chamber 28. Interior chamber 28 is interrupted by at least one and preferably a plurality of regions 30 in which sheet 24 is laminated to sheet 26 within the confines of the outer perimeter of chamber 28, thereby dividing chamber 28 into a plurality of chamber regions that are fluidly coupled to one another within the confines of the overall chamber 28. Joined regions 30 of graft material are thereby fluidly isolated from the volume defined by compartment 28. Preferably, within joined regions 30 there are provided thru-holes 32 such as slits, perforations or other openings, which define passages through both sheets 24 and 26 in the laminated regions 30. In this manner, thru-holes 32 can allow for the passage of fluids, such as bodily liquids, from one side of graft body 20 to another opposite side of graft body 20. At the same time, because joined regions 30 fluidly isolate the thru-holes 32 from the interior volume of chamber 28, the presence of thru-holes 32 does not cause leakage of fluids received in chamber 28 from the graft body 20. In the illustrated embodiment this is accomplished by providing a peripheral region 34 of the joined region 30 that surrounds the thru-hole 32 and isolates the thru-hole 32 from the interior chamber 28. In these peripheral regions 34, the sheets 24 and 26 are sufficiently laminated to one another to fluidly isolate thru-holes 32 from the volume of chamber 28.

Chamber 28 has an outer periphery 36 defined at the boundary between joined and unjoined regions of sheets 24 and 26. In the illustrated embodiment, this periphery is shown as being substantially circular although it will be understood that other shapes such as polygonal or curved shapes may also be used. Chamber 28 and other chambers in grafts herein may be formed in any suitable fashion, e.g. by molds that selectively compress on areas of stacked ECM or other sheets to bond the sheets to one another (e.g. by dehydrothermal bonding during drying by lyophilization or otherwise, crosslinking with chemical or other agents, bonding agents, or other bonding techniques) in those compressed areas while leaving an internal region of the sheets unlaminated to form a chamber, by casting material to form a chamber, or otherwise. During formation of the chamber in the graft material, the chamber may be filled with a substance that is removable after formation of the chamber. This substance may for example be a frozen volume of a liquid such as water that can be removed for example by sublimation during lyophilization, a packing material such as Teflon sheet(s) or strip(s) that can be removed from the chamber after its formation, or another suitable material.

Graft body 20 also includes an open tubular passage 38 extending from an opening 40 at the outer periphery of graft body 20 to an opening 42 opening into chamber 28. This passage 38 can be used for example to pass fluids into chamber 28 and/or to receive a cannula for passing fluids into chamber 28. Graft body 20 generally includes a peripheral laminated region 44 in which sheets 24 and 26 are joined to one another, which fluidly isolates chamber 28 from the outer periphery 46 of the graft body 20. Passage 38 interrupts this fluid isolation and thus fluidly communicates between outer opening 40 and inter opening 42. The laminated periphery 44 includes uninterrupted joined regions of varying width including lateral laminated regions 48 and 50 and upper and lower laminated regions 52 and 54. Graft body 20 also includes open tubular passages 56 and 58 generally located within laminated periphery 44. Passage 56 resides between laminated region 50 and an outermost laminated region 60, and passage 58 resides between laminated region 48 and outermost laminated region 62. Passage 56 includes a first opening 64 communicating through passage 58 with a second opening 66. Passage 58 includes a first opening 68 communicating through passage 58 with second opening 70. Passages 56 and 58 do not communicate with internal chamber 28 but rather are fluidly isolated therefrom. As will be discussed again later, passages 56 and 58 are for receiving elongated extensions of a handle structure which can be useful for support and/or transfer operations for the graft body 20. The peripheral laminated region 44 may also have a plurality of thru-holes therein, for example similar to thru-holes 32, e.g. to allow passage of biological fluid through graft body 20 in this region. As illustrated, the outer periphery of graft body 20 is generally curved but is interrupted by generally straight portions at regions 72, 74, 76 and 78 provided at openings 64, 68, 70 and 66 respectively, with regions 72 and 78 generally running parallel to one another and likewise for regions 74 and 76.

Figure 4:
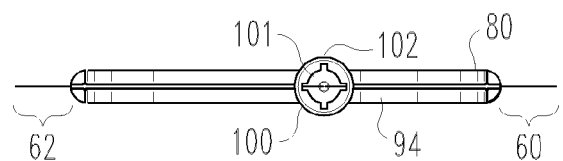
FIG. 4 provides a top end view of the handle structure/graft material combination of FIG. 3.
Figure 3:
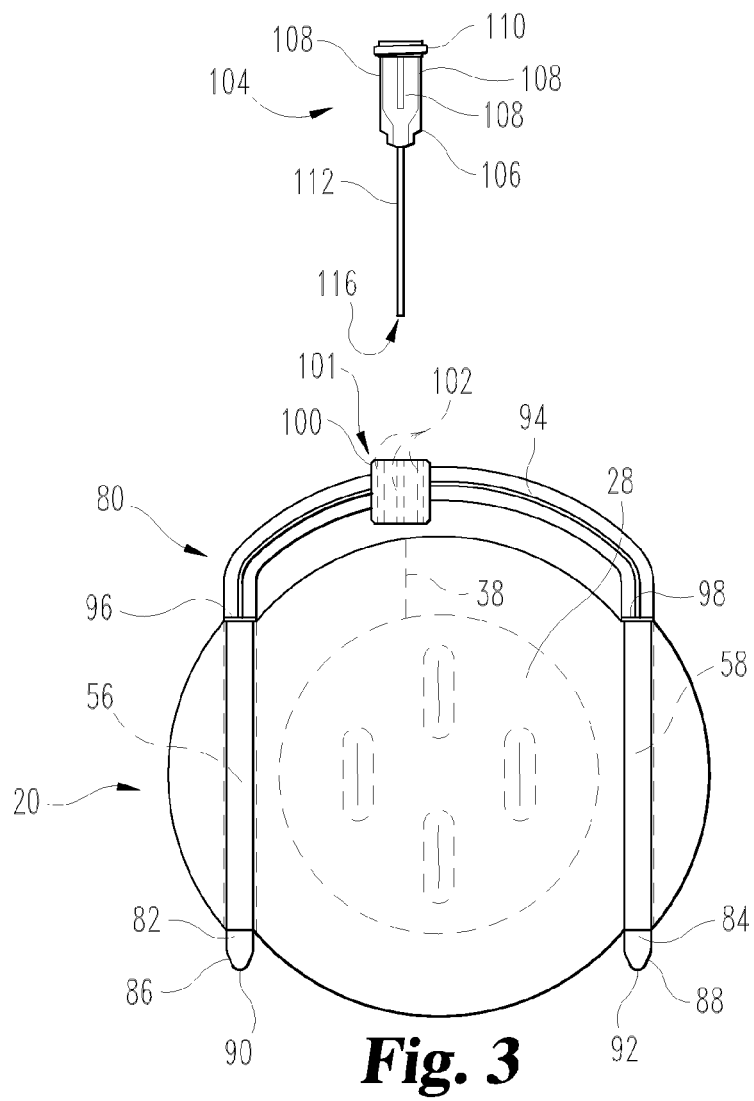
FIG. 3 provides a top view of the graft material embodiment of FIG. 1 in combination with a removable handle structure also defining a receiver, and a liquid input device for receipt in the receiver.
Figure 5:
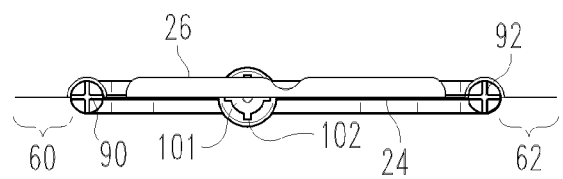
FIG. 5 provides a bottom end view of the handle structure/graft material combination of FIG. 3.

Referring now more particularly to FIGS. 3-5 shown is graft body 20 assembled together with a handle structure 80. Handle structure 80 includes a first prong 82 and second prong 84 which are received in passages 56 and 58 of graft body 20 respectively. First prong 82 includes a tapering region 86 and second prong 84 includes a corresponding tapering region 88, terminating in generally rounded tips 90 and 92 respectively. Handle structure 80 includes a connecting portion 94 connecting prongs 82 and 84. As illustrated, connecting portion 94 is a generally smoothly curved region providing handle structure 80 overall as a "U" shaped member. Handle structure 80 also defines a first outwardly extending annular shoulder 96 and a second outwardly extending annular shoulder 98. Shoulders 96 and 98 have a diameter or other outermost dimension that exceeds the diameter or outermost dimension of passages 56 and 58 and thereby provide stops which resist further travel of prongs 82 and 84 through passages 56 and 58 respectively. Handle structure 80 also includes an attached receiver 100 for receiving a securing a fluid input element 104. Receiver 100 defines a thru-opening 101 and a plurality of notches 102. Thru-opening 101 is generally axially aligned with passage 38 and graft body 20. Fluid input element 104 includes a proximal hub 106 that defines a plurality of raised shoulders 108 which are aligned with and received within notches 102 to secure element 104 within opening 101 in non-rotatable fashion. Hub 106 includes a proximal coupling region 100 which can for example carry threads or other arrangements, e.g. as provided by a luer-lock connector, for coupling to a liquid injection device such as a syringe. Fluid input element 104 also includes an input cannula 112 attached to hub 106 and arranged to receive and transfer fluids from the hub 106 to a distal opening 116. Cannula 112 is sized for receipt within passage 38 when hub 106 is engaged and secured in opening 101 of receiver 100, preferably with distal opening 116 residing within chamber 28.

Figure 6:
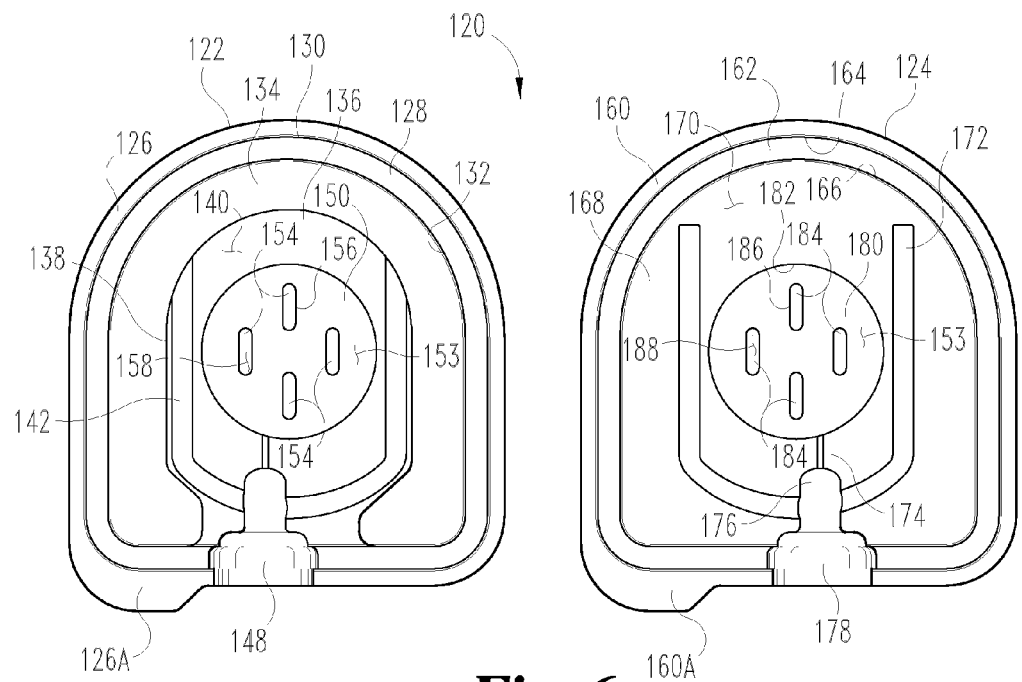
FIG. 6 provides a top view of the internal features of first and second mating tray portions configured to receive the handle structure/graft material combination of FIGS. 3 to 5.

Referring now particularly to FIG. 6, shown is a tray 120 that can be used with the assembly provided by handle structure 80, graft body 20 and fluid input element 104. Tray 120 includes a lower portion 122 and an upper portion 124. Lower and upper tray portions 122 and 124 are generally designed to cooperate with one another to receive and support such an assembly. Lower portion 122 includes a peripheral flange 126 and an upstanding shoulder 128 located inward thereof and designed to frictionally mate with a groove 162 defined in upper tray portion 124 as will be discussed later, for example to provide a snap fit. Upstanding shoulder 128 has an outer wall 130 extending upwardly from flange region 126 and an inter wall 132 opposite the outer wall 130. Positioned inward of shoulder 128 is an internal well 134 which extends around a central region 136 upstanding from well 134 and designed to accommodate the graft body 20/handle structure 80 assembly discussed above. Upstanding central region 136 includes an outer wall 138 and an upper surface 140. A generally "U" shaped groove 142 is defined in upper surface 140, corresponding in shape to the handle structure 80. Upper surface 136 also has defined therein a groove 144 sized to receive and retain the cannula 112 of fluid input element 104. Also defined within upper surface 140 is a generally semi-annular depression 146 for accommodating receiver 100 of handle structure 80. To the outward or peripheral side of depression 146 is another, larger general semi-annular hollow 148 designed to accommodate the distal end of an input device such as a syringe barrel (see e.g. FIG. 8, discussed below).

Surface 140 of central region of 136 also defines a central well sized to receive and accommodate the compartment 29 of graft body 20. Central well 150 has an outer wall 152 and a lower surface 153. Upstanding from lower surface 153 are a plurality of pedestals 154 having outer walls 156 and upper surfaces 158. As can be seen, upper surfaces 158 of pedestals 154 are sized and shaped generally to correspond to the size and shape of the joined regions 32 that divide chamber 28 of graft body 20.

Upper tray portion 124 includes a peripheral flange 160 which generally corresponds to flange portion 126 of lower tray portion 122. Inward of flange 160 lies a groove 162 having an outer wall 164 and an inner wall 166. As discussed above, groove 162 cooperates with shoulder 128 of lower tray portion 122 in the secure, friction-fit closure of the overall tray 120. For these purposes the outer and inner walls 130 and 132 of tray portion 122 can frictionally engage the outer and inner walls 164 and 166 of upper tray portion 124. Inward of groove 162 is a raised central region 168 having an upper surface 170. Upper surface 170 has a generally "U" shaped groove 172 defined herein, which cooperates with groove 142 of lower tray portion 122 to accommodate and support handle structure 80. A generally semi-annular hollow 176 is also defined from upper surface 170, which cooperates with hollow 146 of lower tray portion 122 to accommodate and support receiver 100 of handle structure 80. Peripheral to hollow 176 is a generally larger semi-annular hollow 178, which cooperates with hollow 148 of lower tray portion 122 to accommodate the distal end region of and end put device such as a syringe, as discussed above.

A central well 180 is defined in upper surface 170, corresponding in size and shape to central well 150 of lower tray portion 122. Well 180 includes an outer peripheral wall 182 and a lower surface 183. Upstanding from lower surface 183 are a plurality of pedestals 184 having outer walls 186 and upper surfaces 188. As can be seen, pedestals 184 are similar in size and shape to pedestals 154 of lower tray portion 122, and positioned to be in registry therewith when tray portions 122 and 124 are mated together. Pedestals 184 and 154 can contact and compress the graft body 20 on opposite sides thereof when the upper and lower tray portions 122 and 124 are mated together so as to compress joined regions 32 of graft body 20. This can serve to support joined regions 32 during the application of liquids into chamber 28, for instance providing resistance to potential separation (e.g. delamination) of sheets 24 and 26 in joined regions 32. In similar fashion, portions of surface 140 of tray portion 122 can cooperate with portions of surface 170 of tray portion 124 to compress the graft body 20 when the tray portions 122 and 124 are mated together over graft body 20, including in regions outside and around the periphery 36 of chamber 28, and in regions adjacent passage 38. This can again support the graft material in these regions and provide resistance to separation of sheets 24 and 26 during handling or during introduction of liquids into passage 38 and/or chamber 28, thus maintaining the integrity of the passage 38 and chamber 28. It will be understood that such compression by a tray enclosure in selective regions can be provided even in the case of graft bodies 20 or portions thereof which are not laminated structures (for example homogenous cast, molded or formed structures), and that the compression can nonetheless help to maintain the structural integrity of the graft material and/or can aid in directing patterns of flow during the application of liquids to the graft material.

Figure 7:
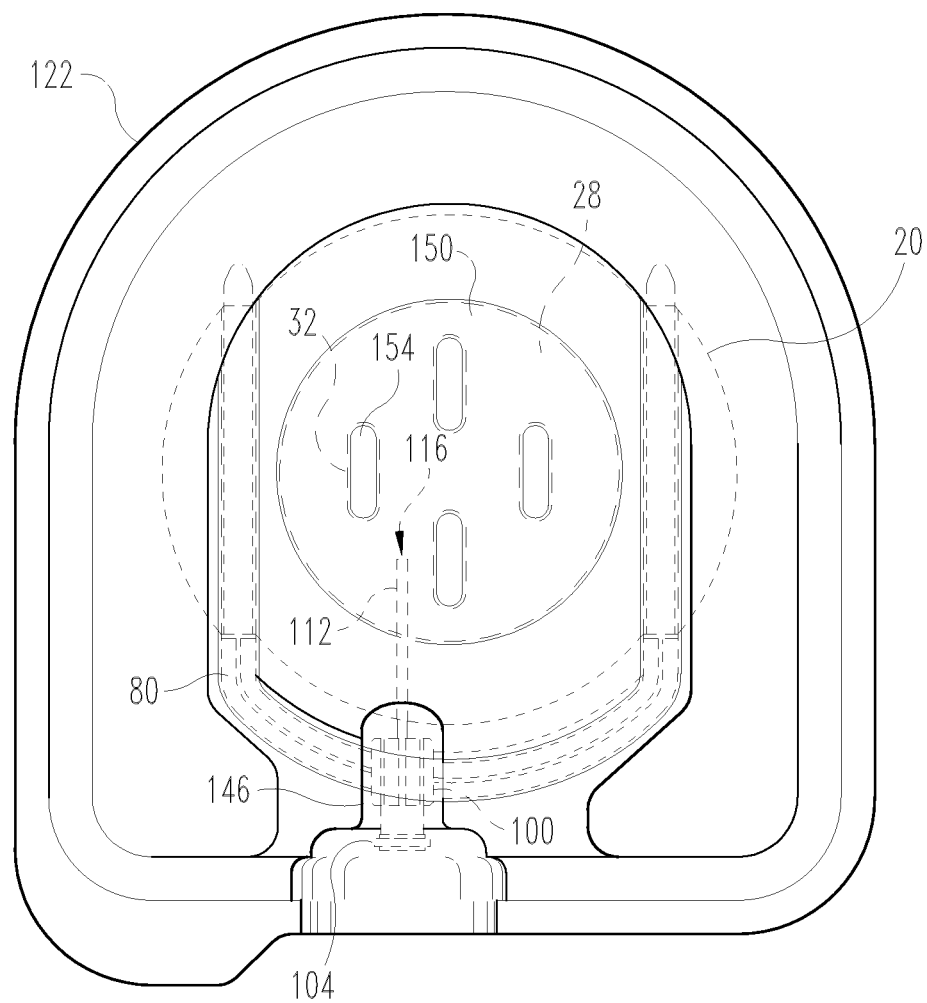
FIG. 7 provides a top view of one of the tray portions of FIG. 6 having received thereon the handle structure/graft material combination of FIGS. 3 to 5.

FIG. 7 shows a view of lower tray portion 122 with the assembly including graft body 20, handle structure 180 and fluid input element 104 received thereon. As can be seen, the central region 136 receives and accommodates graft body 120 with the chamber 28 of graft body 20 aligned with well 150 of tray portion 122. As well, handle structure 80 as received and accommodated within groove 142, receiver 100 is received and accommodated in hollow 146, and joined regions 32 of graft body 20 are received over and aligned with pedestals 154. Further, in the assembled structure, fluid input element 104 is received within the opening 101 of receiver 100 with cannula 112 received thru passage 38 of graft body 20 having its distal opening 116 received within chamber 28 of graft body 20.

Figure 8:
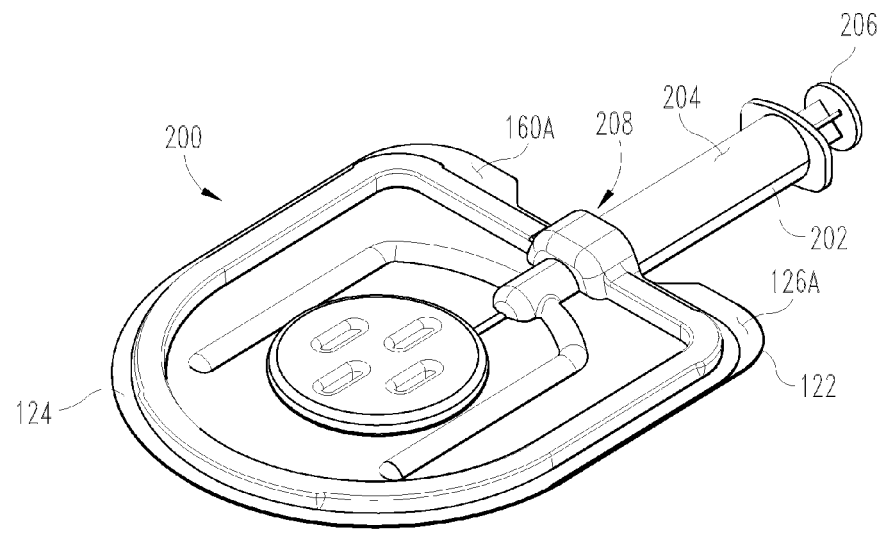
FIG. 8 provides a perspective view of the assembled graft material apparatus of the components illustrated in FIGS. 1 to 7, in combination with a syringe coupled to the liquid input device of FIG. 3.

With reference to FIG. 8, shown is medical graft system 200 that includes tray portions 122 and 124 assembled to provide tray 120 having modifiable graft 20 received therein (not visible). With the tray 120 so assembled, the tray 120 can compress selected regions of the graft body 20 as discussed above. Additionally, a fluid injection device 202, such as a syringe as illustrated, is fluidly coupled to fluid element 104 which in turn is received thru passage 38 in graft 20 having its distal opening 116 positioned within chamber 28 of graft 20. The fluid connection of fluid delivery device 202 with fluid delivery element 104 can be by any suitable means including by a threaded connection between device 202 and threaded proximal end 110 of hub 106, for example as provided by a luer-lock connection. Device 202 can include a syringe barrel 204 and a plunger 206 received therein and operable to advance within barrel 204 so as to dispel fluids from a distal tip region 208. In system 200, upon transfer of fluids from device 202 through fluid delivery element 104 and into chamber 28, materials such as cells or other suspended particulates, or solutes, can be introduced into chamber 28 and can at least in part deposit upon or within at least portions of graft body 22. In certain embodiments, the graft material is liquid permeable, and at least a portion of the liquid or other applied fluid can transfer thru the material of graft body 22, such as sheets 24 and/or 26, and be drained by gravity or otherwise into the capture well formed by well 150 and well 180. In addition or alternatively, the material of graft body 22 such as that of sheets 24 and 26 can be flexible or compliant such that the passage of fluids into compartment 28 inflates chamber 28 to a larger dimension. During or after this inflation process, fluids transferred into chamber 28 can at least in part transfer through the graft material, but at a rate slower than their introduction into compartment 28, such that compartment 28 is inflated. The graft material of graft body 20 can be of sufficiently pliant when wet that when administered to the patient, the upper and lower walls of chamber 28 collapse against one another to flatten the graft body 20, optionally to essentially a flat sheet graft.

In a further use operation, after the transfer of fluids or materials into chamber 28, the upper tray portion 124 can be separated from the lower tray portion 122, for example using tab regions 126A and/or 160A. Where liquid has drained into well 150, lower tray portion 122 may be maintained in a relatively level condition to retain the fluids by gravity within well 150. The modified graft 20 can be lifted out of lower tray portion 122, for example using fluid input device 202 (if still connected) and/or using fluid input element or handle structure 80. After this, the graft 20 can be transferred to a region of the patient in need of graft 20, for example an ulcer or other topically-exposed wound on the patient. Graft 20 can then be separated from handle structure 80, with this separation achieved by cutting the graft body 20 and/or by withdrawing the prongs 82 and 84 from passages 56 and 58 of graft body 20. During or after this operation, if needed, the graft body 20 can be cut to size by the attending health care provider. It will be understood that the fluid input device 202 and/or the fluid input element 104 can be removed from their connection with handle structure 80 at any suitable time during or after a transfer of the graft 20 to the patient.

Figure 9:
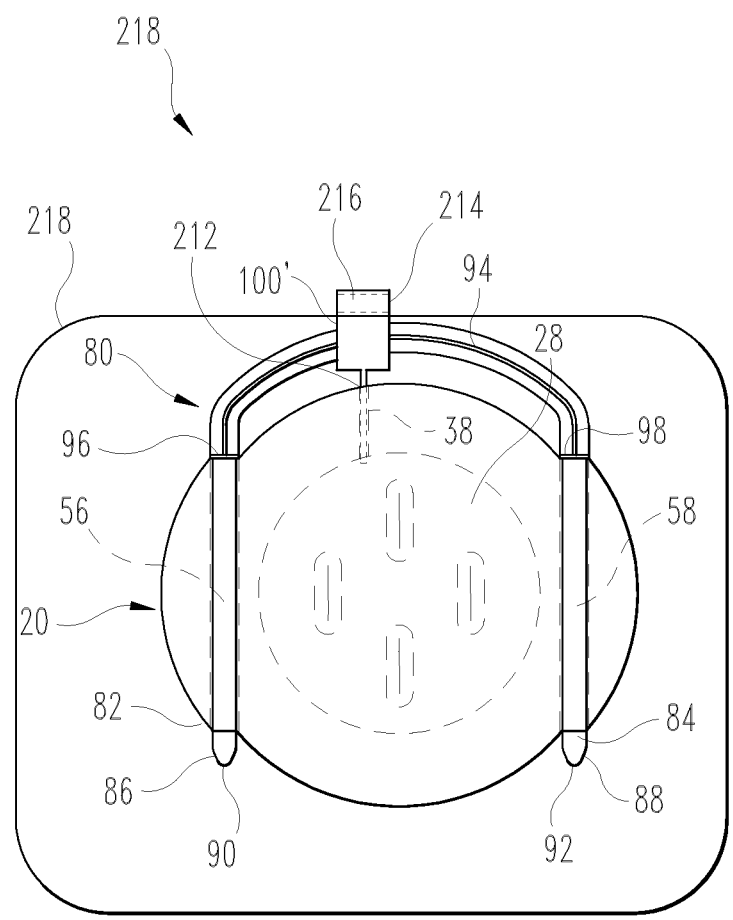
FIG. 9 illustrates another embodiment of a medical graft apparatus.

With reference to FIG. 9, shown is another embodiment of a medical graft system 210. Graft system 210 includes a graft assembly as shown in FIG. 3, which has components similarly numbered in FIG. 9. However, the handle structure 80 includes a modified receiver 100' which is extended in length relative to receiver 100 of FIG. 3 and provides a tubular passage for delivery of flowable material into the graft body 20. Receiver 100' includes a tubular extension 212 with an internal lumen extending through passage 38 of graft body 20 for delivery of liquid to chamber 28. Receiver 100' also includes an extended region 214 residing outside of graft body 20 and which houses a needle-penetrable, resealable septum 216. It will be understood that the overall tubular passage defined by receiver 100 can be a single integral piece or may be multiple connected pieces. System 210 also includes a sterile enclosure 218 such as a polymer film or other package, in which graft body 20 and at least a portion of the combined receiver 100'/handle 80 structure is sterilely enclosed. It will be understood that in other embodiments the tubular passage-providing receiver and handle may be separate pieces (unattached to one another), in which case at least a portion of the receiver, and potentially only a portion thereof, and at least a portion of the handle, and potentially only a portion or all of the handle, can be sterilely enclosed within the sterile enclosure. Septum 216 can be exposed exterior of the sterile enclosure 218 and when so positioned also provides a sterile seal within the tubular passage of receiver 100' to maintain sterility within the sterile enclosure 218. For these purposes the material of the sterile enclosure 218 may be bonded to or otherwise sealed around a periphery of receiver 100'. The entire system 210 can also be sterilely packaged within a second sterile enclosure such as a polymer film or other package for purposes of storage, handling and/or shipping, if desired. Conventional sterilization processes such as radiation or ethylene oxide sterilization may be used for these purposes. Similar sterile enclosure(s) and sterilization methodology can be used for all embodiments disclosed and encompassed herein.

In use, to deliver a liquid or other flowable additive, such as any of those described herein, into chamber 38 of graft body 20, a needle with an attached syringe can be used to penetrate septum 216, and the additive injected into the internal region of the receiver 100' so as to pass through tubular extension 212 and into chamber. Passage of the needle through the septum 216 and subsequent removal of the needle from the septum 216 maintains the sterility of the environment within sterile enclosure 218. If desired, and especially in the case of a cellular composition added to the graft body 20, the resulting graft body 20 can be incubated for a period of time to allow for attachment and/or proliferation of the added cells. In certain modes, the graft body with the cells or other additive is incubated at physiologic temperatures, for example about 37 to about 38° C., for a period of up to about 12 hours, for example about 1 to about 3 hours.

Whether the system 210 has been incubated or not, when desired, the sterile enclosure 218 can be removed and the graft body 20 can be delivered to a graft site of a patient. This may include use of the handle structure 80 to assist in placing the graft body, as discussed herein, and subsequent removal of the handle structure 80 from the graft body 20. In this regard, while the handle structure 80 depicted in the preferred, illustrated embodiments is slidably removable from the graft body 20, other arrangements can be used, including for example a bonding or other permanent attachment of the handle structure to a region (e.g. the periphery) of the graft body, and unneeded portions of the graft body can be cut to separate the handle structure from the graft body portion(s) to remain at the patient site to be treated.

Graft Materials for Use in Inventive Embodiments

In some embodiments, graft materials of and used in the invention comprise extracellular matrix (ECM) tissue, beneficially in the form of an isolated, decellularized ECM tissue layer. The ECM tissue can be obtained from a warm-blooded vertebrate animal, such as an ovine, bovine or porcine animal. For example, suitable ECM tissue include those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. ECM tissues comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. Porcine tissue sources are preferred sources from which to harvest ECM tissues, including submucosa-containing ECM tissues.

ECM tissue when used in the invention is preferably decellularized and highly purified, for example, as described in U.S. Pat. No. 6,206,931 to Cook et al. or U.S. Patent Application Publication No. US2008286268 dated Nov. 20, 2008, publishing U.S. patent application Ser. No. 12/178,321 filed Jul. 23, 2008, all of which are hereby incorporated herein by reference in their entirety. Preferred ECM tissue material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 or U.S. Patent Application Publication No. US2008286268 may be characteristic of any ECM tissue used in the present invention.

In certain embodiments, the ECM tissue material used as or in the graft material will be a membranous tissue with a sheet structure as isolated from the tissue source. The ECM tissue can, as isolated, have a layer thickness that ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue material utilized desirably retains a structural microarchitecture from the source tissue, including structural fiber proteins such as collagen and/or elastin that are non-randomly oriented. Such non-random collagen and/or other structural protein fibers can in certain embodiments provide an ECM tissue that is non-isotropic in regard to tensile strength, thus having a tensile strength in one direction that differs from the tensile strength in at least one other direction.

The ECM tissue material may include one or more bioactive agents native to the source of the ECM tissue material and retained in the ECM tissue material through processing. For example, a submucosa or other remodelable ECM tissue material may retain one or more native growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain from the source tissue one or more bioactive components that induce, directly or indirectly, a cellular response such as a change in cell morphology, proliferation, growth, protein or gene expression.

Submucosa-containing or other ECM materials used in the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material used in the invention. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Inventive graft compositions herein can incorporate xenograft ECM material (i.e., cross-species material, such as tissue material from a non-human donor to a human recipient), allograft ECM material (i.e., interspecies material, with tissue material from a donor of the same species as the recipient), and/or autograft ECM material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM tissue material will be xenogenic relative to the patient receiving the graft, and any added cells or other exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human cells and/or serum proteins and/or other material(s) as described herein, those exogenous materials being naturally derived and/or recombinantly produced.

When used in the invention, ECM materials can be free or essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

In additional embodiments, substrates of the invention can be made from ECM's or other collagenous materials that have been subjected to processes that expand the materials. In certain forms, such expanded materials can be formed by the controlled contact of an ECM material with a denaturing agent such as one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a substrate. Illustratively, the expanded material can be enriched with bioactive components, comminuted, dried, and/or molded, etc., in the formation of a substrate of a desired shape or configuration. In certain embodiments, a dried substrate formed with the expanded ECM material can be highly compressible and/or expandable.

Treatment of an ECM material with a denaturant, such as an alkaline material, can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. It will be apparent to one skilled in the art that the magnitude of the expansion is related to several factors, including for instance the concentration or pH of the alkaline medium, the exposure time of the alkaline medium to the material, and temperature used in the treatment of the material to be expanded, among others. These factors can be varied through routine experimentation to achieve a material having the desired level of expansion, given the disclosures herein.

A collagen fibril is comprised of a quarter-staggered array of tropocollagen molecules. The tropocollagen molecules themselves are formed from three polypeptide chains linked together by covalent intramolecular bonds and hydrogen bonds to form a triple helix. Additionally, covalent intermolecular bonds are formed between different tropocollagen molecules within the collagen fibril. Frequently, multiple collagen fibrils assemble with one another to form collagen fibers. It is believed that the addition of an alkaline substance to the material as described herein can be conducted so as to not significantly disrupt the intramolecular and intermolecular bonds, but denature the material to an extent that provides to the material an increased processed thickness, e.g. at least twice the naturally-occurring thickness. ECM materials that can be processed to make expanded materials for use as substrates can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness. The expanded ECM material can then be processed to provide foam or sponge substrates, e.g. by comminuting, casting, and drying the processed material. Additional information concerning expanded ECM materials and their preparation is found in United States Patent Application Publication No. US20090326577 published Dec. 31, 2009, publishing U.S. patent application Ser. No. 12/489,199 filed Jun. 22, 2009, which is hereby incorporated herein by reference in its entirety.

In addition to or as an alternative to ECM materials, the graft material used in the invention may be comprised of other suitable materials. Illustrative materials include, for example, synthetically-produced substrates comprised or natural or synthetic polymers. Illustrative synthetic polymers can include nonresorbable synthetic biocompatible polymers, such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof; or resorbable synthetic polymer materials such as polylactic acid, polyglycolic acid or copolymers thereof, polyanhydride, polycaprolactone, polyhydroxy-butyrate valerate, polyhydroxyalkanoate, or another biodegradable polymer or mixture thereof. Preferred graft materials comprised of these or other materials will be porous matrix materials configured to allow cellular invasion and ingrowth into the matrix.

Extracellular matrix tissue layers can be used in the manufacture of laminated graft body structures, such as that illustrated in graft body 20 illustrative above. For these purposes, each of sheet 24 and 26 can for example be comprised of about 1 to about 10 extracellular matrix tissue layers. Illustratively, either of sheet 24 and 26 can include only a single extracellular matrix tissue layer, and the other may include multiple (e.g. 1 to 10, or 2 to 6) extracellular matrix tissue layers. Sheets of multilaminate ECM tissue layers can be prepared in any suitable fashion. These include, for instance, dehydrothermal bonding under heated, non-heated or lyophilization conditions, using adhesives, glues or other bonding agents, crosslinking with chemical agents or radiation (including UV radiation), or any combination of these with each other or other suitable methods. For additional information as to techniques for laminating ECM layers to one another, reference may be made for example to U.S. Pat. Nos. 5,711,969, 5,755,791, 5,855,619, 5,955,110, 5,968,096, and to U.S. Patent Publication No. 20050049638. Further, where sheets 24 and 26 are laminated to one another, these same techniques may for example be used. The lamination of layers within sheets 24 and 26 and the lamination of selected regions of sheets 24 and 26 to one another can also be accomplished simultaneously using these or other suitable procedures.

In certain embodiments, sheets 24 and 26 are laminated in selected regions, e.g. as discussed above for graft body 20, using a preparative procedure with a two-piece mold. In such a procedure, sheets 24 and 26 can be provided in a wetted condition. Sheet 26 can be laid upon and pressed into a first mold piece having a surface contour which is the same or approximately the same as the graft-accommodating region of tray portion 122. Thus, sheet 26 can be tucked into and around a well and pedestals of the first mold piece that match the well 150 and pedestals 154 of tray portion 122, and into a "U" shaped groove that matches groove 142 of tray portion 122. The handle structure 80 and the cannula 112, pieces having matching structures and dimensions, can then be laid onto sheet 26. Sheet 24 can then be laid onto this assembly, and for example pulled fairly taught (e.g. to result in the flat upper sheet 24 as depicted in graft body 20, along with the tufted lower sheet 26. A second mold piece having a surface contour including grooves that match groove 172 and groove 174 of tray portion 124, and which compresses other areas of the sheets 24 and 26 to be joined, is then clamped over the first mold piece. The first and second mold pieces, when so clamped, compress the sheets 24 and 26 against one another where they are to be laminated together, and do not compress the sheets 24 and 26 in other areas. The clamped mold assembly can then be dried, preferably by lyophilization. This can be used to provide a dried graft body 20 in which the ECM tissue in the laminated areas is less porous (and/or more dense) than the ECM tissue in the non-laminated areas. If desired, after clamping the mold over the wetted sheets 24 and 26 and prior to drying, a liquid such as water can be injected into the chamber 28 to inflate and assure separation of the walls defining it, to reduce the risk of unintended lamination of these walls to one other in the region intended for chamber 28 during the drying process. The mold can be provided with an injection port and drain holes to facilitate these processes. After drying the assembly can be deconstructed to obtain the graft body 20 or a precursor that can be trimmed of excess material to provide the shape of graft body 20.

Cells and/or Other Therapeutic Substances For Use in Inventive Embodiments

Any one or any combination of a wide variety of cell types can be applied to graft materials as disclosed herein to provide cellular graft compositions and methods of the invention. For example, the cells can be skin cells, skeletal muscle cells, cardiac muscle cells, lung cells, mesentery cells, or adipose cells. The adipose cells may be from omental fat, properitoneal fat, perirenal fat, pericardial fat, subcutaneous fat, breast fat, or epididymal fat. In certain embodiments, the cells comprise stromal cells, stem cells, or combinations thereof. As used herein, the term "stem cells" is used in a broad sense and includes traditional stem cells, adipose derived stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Additional illustrative cells which can be used include hepatocytes, epithelial cells, Kupffer cells, fibroblasts, neurons, cardiomyocytes, myocytes, chondrocytes, pancreatic acinar cells, islets of Langerhans, osteocytes, myoblasts, satellite cells, endothelial cells, adipocytes, preadipocytes, biliary epithelial cells, and progentior cells of any of these cell types.

In some embodiments, the cells incorporated in the cellular grafts are, or include, endothelial progenitor cells (EPCs). Preferred EPCs for use in the invention are endothelial colony forming cells (ECFCs), especially ECFCs with high proliferative potential. Suitable such cells are described for example in U.S. Patent Application Publication No. 20050266556 published Dec. 1, 2005, publishing U.S. patent application Ser. No. 11/055,182 filed Feb. 9, 2005, and U.S. Patent Application Publication No. 20080025956 published Jan. 1, 2008, publishing U.S. patent application Ser. No. 11/837,999, filed Aug. 13, 2007, each of which is hereby incorporated by reference in its entirety. Such ECFC cells can be a clonal population, and/or can be obtained from umbilical cord blood of humans or other animals. Additionally or alternatively, the endothelial colony forming cells have the following characteristics: (a) express the cell surface antigens CD31, CD105, CD146, and CD144; and/or (b) do not express CD45 and CD14; and/or (c) ingest acetylated LDL; and/or (d) replate into at least secondary colonies of at least 2000 cells when plated from a single cell; and/or (e) express high levels of telomerase, at least 34% of that expressed by HeLa cells; and/or (f) exhibit a nuclear to cytoplasmic ratio that is greater than 0.8; and/or (g) have cell diameters of less than about 22 microns. Any combination of some or all of these features (a)-(g) may characterize ECFCs used in the present invention.

In other embodiments, the cells incorporated in the cellular grafts are, or include, muscle derived cells, including muscle derived myoblasts and/or muscle derived stem cells. Suitable such stem cells and methods for obtaining them are described, for example, in U.S. Pat. No. 6,866,842 and U.S. Pat. No. 7,155,417, each of which is hereby incorporated herein by reference in its entirety. The muscle derived cells can express desmin, M-cadherin, MyoD, myogenin, CD34, and/or Bcl-2, and can lack expression of CD45 or c-Kit cell markers.

In still other embodiments, the cells incorporated in the cellular grafts are, or include, stem cells derived from adipose tissue. Suitable such cells and methods for obtaining them are described for example in U.S. Pat. No. 6,777,231 and U.S. Pat. No. 7,595,043, each of which is hereby incorporated herein by reference in its entirety. The cellular population can include adipose-derived stem and regenerative cells, sometimes also referred to as stromal vascular fraction cells, which can be a mixed population including stem cells, endothelial progenitor cells, leukocytes, endothelial cells, and vascular smooth muscle cells, which can be adult-derived. In certain forms, cellular grafts of the present invention can be prepared with and can include adipose-derived cells that can differentiate into two or more of a bone cell, a cartilage cell, a nerve cell, or a muscle cell.

In addition to or as an alternative to cells, a liquid or otherwise flowable additive to be added to the graft can include other therapeutic substances. These substances may for example include growth factors, pharmaceutical agents, biologic materials or extracts such as platelets or platelet rich plasma, platelet lysates, blood or bone marrow fractions, and/or extracellular matrix particles or gels that optionally retain biologically active substances native to their source tissue such as growth factors, glycosaminoglycans, and/or proteoglycans. These and still other therapeutic substances known to those skilled in the art can be delivered into an internal chamber of the graft e.g. as described herein.

Medical Treatments with Grafts

Grafts of and prepared in accordance with the invention can be used in a wide variety of clinical applications to treat damaged, diseased or insufficient tissues, and can be used in humans or in non-human animals. Such tissues to be treated may, for example, be muscle tissue, nerve tissue, brain tissue, blood, myocardial tissue, cartilage tissue, organ tissue such as lung, kidney or liver tissue, bone tissue, arterial or venous vessel tissue, skin tissue, and others.

In certain embodiments, the grafts can be used to enhance the formation of blood vessels in a patient, for example to alleviate ischemia in tissues. Direct administration of blood vessel-forming cellular grafts, for example grafts containing endothelial colony forming cells or other endothelial progenitor cells, to an ischemic site can enhance the formation of new vessels in the affected areas and improve blood flow or other outcomes. The ischemic tissue to be treated may for example be ischemic myocardial tissue, e.g. following an infarction, or ischemic tissue in the legs or other limbs such as occurs in critical limb ischemia.

The grafts of the invention can also be used to enhance the healing of partial or full thickness dermal wounds, such as skin ulcers, e.g. diabetic ulcers, and burns. Illustratively, the administration of grafts containing cells, for example endothelial colony forming cells or other endothelial progenitor cells, to such wounds can enhance the healing of the wounds.

In other applications, the grafts can be used to generate muscle tissue at a target site, for example in the treatment of skeletal muscle tissue, smooth muscle tissue, myocardial tissue, or other tissue. Illustratively, grafts of the invention containing muscle derived myoblasts can be implanted into muscle tissue of a sphincter such as a urinary bladder sphincter to treat incontinence.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A medical graft for administration to a patient, comprising:
    a graft material having a first outer surface and a second outer surface, the graft material defining an internal chamber between the first outer surface and the second outer surface of the graft material;
    at least one region of the graft material interrupting the chamber and surrounded by the chamber; and
    a thru-hole defined in said at least one region of the graft material, the thru-hole extending between the first outer surface and the second outer surface of the graft material, wherein a peripheral portion of the at least one region of the graft material surrounds the thru-hole and isolates the thru-hole from the internal chamber, and further wherein the thru-hole allows passage of biological fluids of the patient from one side of the graft material to another side of the graft material when the graft material is administered to the patient;
    wherein a first wall of the graft material defines a first boundary of the chamber;
    wherein a second wall of the graft material defines a second boundary of the chamber;
    wherein the first and second walls are laminated to one another to provide said at least one region of the graft material; and
    wherein the first wall and the second wall comprise an extracellular matrix material.

2. The medical graft of claim 1, wherein the thru-hole comprises an elongate slit extending between the first outer surface and the second outer surface of the graft material.

3. The medical graft of claim 1, wherein the graft material comprises a matrix for supporting cell growth.

4. The medical graft of claim 1, comprising a plurality of said regions.

5. The medical graft of claim 4, wherein each of said regions defines a thru-hole.

6. The medical graft of claim 1, also comprising a peripheral flange defined by the graft material, the peripheral flange extending around said internal chamber.

7. The medical graft of claim 6, also comprising at least one open passage defined by the graft material of the peripheral flange, the open passage extending through the flange and opening into the internal chamber.

8. A medical graft apparatus, comprising:
    a medical graft of claim 1; and
    a tray enclosure in which the graft material is received.

9. The medical graft apparatus of claim 8, wherein the tray enclosure compresses the graft material in selected regions.

10. A medical graft apparatus, comprising:
    a medical graft of claim 1; and
    a sterile enclosure sterilely enclosing the medical graft.

11. A method for preparing a medical graft material, comprising:
    delivering liquid additive to the graft material of a medical graft of claim 1.

12. A medical graft device for administration to a patient, comprising:
    a graft material defining an internal chamber and a peripheral flange around said internal chamber, the graft material comprising a porous matrix material configured to allow cellular invasion and ingrowth into the porous matrix material, the graft material having a first side and a second side, with the first side and the second side defining outermost surfaces of the medical graft device;

a plurality of regions of the graft material interrupting the chamber and surrounded by the chamber, said regions defining portions of said first side and portions of said second side, and said regions being discrete from one another and separated from one another by portions of the chamber;

wherein a first wall of the graft material defines a first boundary of the chamber and a second wall of the graft material defines a second boundary of the chamber;

wherein the first and second walls are bonded to one another to provide said regions of the graft material; and wherein a thru-hole is defined in each of said regions of the graft material, the thru-hole extending between the first side outermost surface and the second side outermost surface of the graft material, wherein a peripheral portion of each of said regions of the graft material surrounds the thru-hole and isolates the thru-hole from the internal chamber, and further wherein the thru-hole allows passage of biological fluids of the patient from one side of the graft material to another side of the graft material when the graft material is administered to the patient.

13. The medical graft device of claim 12, also comprising an open passage defined by the graft material, the open passage extending through the flange and opening into the internal chamber, and a cannula removably received in the passage.

14. The medical graft device of claim 13, also comprising a fluid injection device fluidly coupled to said cannula.

15. A medical graft apparatus, comprising:
a tray enclosure;
a medical graft device according to claim 12 received in the tray enclosure; and
wherein the tray enclosure compresses the graft material of the medical graft device in selected areas.

16. The medical graft apparatus of claim 15, wherein said selected areas create a periphery of compressed graft material around an inner region of uncompressed graft material.

17. The medical graft apparatus of claim 16, wherein said inner region comprises said internal chamber of said graft material.

18. The medical graft apparatus of claim 15, wherein said selected areas bound an open passage of said graft material.

19. The medical graft device of claim 12, wherein the porous matrix material comprises an extracellular matrix material.

20. The medical graft device of claim 19, wherein the extracellular matrix material is a remodelable extracellular matrix material.

21. The medical graft device of claim 20, wherein the remodelable extracellular matrix material retains native growth factors from a source tissue for the remodelable extracellular matrix material.

22. The medical graft device of claim 12, wherein the porous matrix material comprises a resorbable synthetic polymeric material.

23. A medical product, comprising:
a medical graft including:
a graft material having a first outer surface and a second outer surface, the graft material defining an internal chamber between the first outer surface and the second outer surface of the graft material;
at least one region of the graft material interrupting the chamber and surrounded by the chamber; and
a thru-hole defined in said at least one region of the graft material, the thru-hole extending between the first outer surface and the second outer surface of the graft material, wherein a peripheral portion of the at least one region of the graft material surrounds the thru-hole and isolates the thru-hole from the internal chamber, and further wherein the thru-hole allows passage of biological fluids of a patient from one side of the graft material to another side of the graft material when the graft material is administered to the patient; and
a liquid additive applied to the graft material, wherein the liquid additive includes cells.

24. A method of treating a patient, comprising:
grafting tissue of the patient with a medical graft material prepared by a method including delivering liquid additive to the graft material of a medical graft, wherein the medical graft comprises:
the graft material having a first outer surface and a second outer surface, the graft material defining an internal chamber between the first outer surface and the second outer surface of the graft material;
at least one region of the graft material interrupting the chamber and surrounded by the chamber; and
a thru-hole defined in said at least one region of the graft material, the thru-hole extending between the first outer surface and the second outer surface of the graft material, wherein a peripheral portion of the at least one region of the graft material surrounds the thru-hole and isolates the thru-hole from the internal chamber, and further wherein the thru-hole allows passage of biological fluids of the patient from one side of the graft material to another side of the graft material when the graft material is administered to the patient.

25. The method of claim 24, wherein the graft material comprises a porous matrix material configured to allow cellular invasion and ingrowth into the porous matrix material, and wherein the liquid additive includes cells, a growth factor, a pharmaceutical agent, platelets, platelet rich plasma, platelet lysate, a blood fraction, or a bone marrow fraction.

26. The method of claim 25, wherein the porous matrix material comprises an extracellular matrix material.

* * * * *